(12) United States Patent
Gluckman et al.

(10) Patent No.: US 6,365,573 B1
(45) Date of Patent: Apr. 2, 2002

(54) REGULATION OF NEURAL ENZYMES

(75) Inventors: Peter D Gluckman, Remuera; Christopher E. Williams, Grafton; Jian Guan, Avondale, all of (NZ)

(73) Assignee: Neuronz Ltd. (NZ)

( * ) Notice: Subject to any disclaimer, the term of this patent is extended or adjusted under 35 U.S.C. 154(b) by 0 days.

(21) Appl. No.: 09/269,907

(22) PCT Filed: Oct. 6, 1997

(86) PCT No.: PCT/NZ97/00132

§ 371 Date: Jun. 1, 1999

§ 102(e) Date: Jun. 1, 1999

(87) PCT Pub. No.: WO98/14202

PCT Pub. Date: Apr. 9, 1998

(30) Foreign Application Priority Data

Oct. 4, 1996 (NZ) ................................ 299511
Oct. 4, 1996 (NZ) ................................ 299512
Oct. 4, 1996 (NZ) ................................ 299513

(51) Int. Cl.$^7$ ............................................. A61K 31/06
(52) U.S. Cl. ........................................................ 514/18
(58) Field of Search .......................................... 514/18

(56) References Cited

FOREIGN PATENT DOCUMENTS

| AU | A1 38084/93 | 10/1993 |
| EP | A2 0366638 | 5/1990 |
| WO | WO A1 95/17204 | 6/1995 |

OTHER PUBLICATIONS

Sara, V.R. et al. (1989) Indentification of Gly–Pro–Glu (GPE), the aminoterminal tripeptide of insulin–like growth factor 1 which is truncated in brain, as a novel neuroactive peptide, Biochemical and biophysical research Communications, vol. 165, No. 2, Dec. 15, 1989, pp. 766–771.

Nilsson–Hakansson, L.et al. (1993) Effects of IFG–1, truncated IGF–1 and the tripeptide Gly–Pro–Glu on acetylocholine release from parietal cortex of rat brain, NeuroReport, vol. 4, No. 9, Aug. 6, 1993, pp. 1111–1114.

Sara, V.R. et al. (1993) The Biological Role of Truncatted Insulin–like Growth Factor–1 and the Tripeptide GPE in the Central Nervous system, Annals of the New York academy of Sciences, vol. 692, pp. 183–191.

Sara, V.R. et al. (1991) Neuroactive products of IGF–1 and IGF–2 gene expression in the CNS, Molecular Biology and Physiology of Insulin and Insulin like Growth Factors, Editted by Raizada, M.K. and LeRoith, D., Plenum Press, New York, 1991, pp. 439–448.

Gluckman, P.D. et al.(1994) The role of IGF–1 in the response to organ injury–studies in the central nervous system, The insulin–like growth factors and their regulatory proteins, pp. 427–434.

*Primary Examiner*—William R. A. Jarvis
(74) *Attorney, Agent, or Firm*—Heller Ehrman White & McAuliffe LLP

(57) ABSTRACT

This invention relates to the use of the tripeptide Gly-Pro-Glu (GPE) or analogs thereof for the treatment of conditions of the central nervous system (e.g. cerebral vasculitis) in which the amount of the neural enzymes nitric oxide synthetase (NOS) and/or glutamic acid decarboxylase (GAD) is reduced.

18 Claims, 6 Drawing Sheets

REGULATION OF NEURAL ENZYMES

This application is a 371 of PCT/NZ97/00132, filed Oct. 6, 1997.

This invention relates to methods of regulating the effect of neural enzymes. It particularly relates to increasing the effective amount of the neural enzymes choline acetyltransferase (ChAT), glutamic acid decarboxylase (GAD) and nitric oxide synthetase (NOS) in the central nervous system (CNS).

BACKGROUND OF THE INVENTION

GPE is a tripeptide consisting of amino acids Gly-Pro-Glu. It and its dipeptide analogs Gly-Pro and Pro-Glu were first disclosed by Sara et at in EP 0366638. The suggestion made by Sara et al is that GPE has neuromodulatory properties (the capability of affecting the electrical properties of neurons). GPE has also been established as having neuroprotective properties and therefore having utility in the prevention or inhibition of neural cell death (WO 95/17204).

To date however, there has been no teaching or suggestion of GPE or its analogs having any direct effect on the effective amount of neural enzymes present in the CNS. There has certainly been no suggestion of GPE having the ability to upregulate expression of the neural enzymes, ChAT, GAD and NOS, and/or of their receptors.

ChAT is involved in the synthesis of the neurotransmitter acetyl choline. An ability to upregulate ChAT expression therefore has implications for neural, muscular and neuromuscular therapy and prophylaxis, including where the survival of neural cells is not threatened.

GAD is involved in the synthesis of the important inhibitory neurotransmitter gamma amino butyric acid (GABA). An ability to upregulate GAD expression therefore has implications for neural therapy and prophylaxis.

NOS has multiple functions in the brain, including regulating blood flow, cell metabolism and cell survival. An ability to regulate NOS expression using GPE therefore has implications for neural therapy and prophylaxis, including where the survival of neural cells is not threatened.

It is the object of this invention to provide new approaches to neuronal therapy or prophylaxis which involve directly upregulating the expression of neural enzymes present in the CNS, or at least to provide the public with a useful choice.

SUMMARY OF THE INVENTION

In a first aspect, the invention provides a method of treatment of a patient suffering from or susceptible to a condition in which an increase in the amount of a neural enzyme selected from ChAT, NOS and GAD is desirable, which method comprises the step of increasing the effective amount of GPE or an analog thereof within the CNS of said patient.

In a further aspect, the invention provides a method of increasing the amount of the neural enzyme ChAT in a patient for therapy or prophylaxis of a neurological disorder or condition, said method comprising the step of increasing the effective amount of GPE or an analog thereof within the CNS of said patient.

In still a further first aspect, the invention provides a method of increasing the amount of the neural enzyme GAD in a patient for therapy or prophylaxis of a neurological disorder or condition, said method comprising the step of increasing the effective amount of GPE or an analog thereof within the CNS of said patient.

In yet a further aspect, the invention provides a method of increasing the amount of the neural enzyme NOS in a patient for therapy or prophylaxis, said method comprising the step of regulating the effective amount of GPE or an analog thereof within the CNS of said patient.

"Increasing the amount" of a neural enzyme is through upregulation of expression of the neural enzyme.

By "analog" it is meant the dipeptides Gly-Pro and Pro-Glu as well as any other small peptide which is capable of effectively binding to the receptors in the CNS GPE binds to and of inducing an equivalent upregulatory effect upon the expression of ChAT, GAD or NOS and/or their respective receptors.

Most preferably, it is the effective amount of GPE itself which is increased within the CNS of the patient. This can be effected by direct administration of GPE and indeed this is preferred. However, the administration of compounds which indirectly increase the effective amount of GPE (for example a prodrug which, within the patient is cleaved to release GPE) is in no way excluded.

The active compound (GPE or its analog) can be administered alone or, as is preferred, as part of a pharmaceutical composition.

The composition can be administered to the patient peripherally (for example by a parenteral route such as injection into the peripheral circulation) or can be administered directly to the CNS. This latter route of administration can involve, for example, lateral cerebro-ventricular injection or a surgically inserted shunt into the lateral cerebro ventricle of the brain of the patient.

Conveniently, the expression of CHAT and/or its receptors is upregulated through the administration of GPE or its analogs in the prophylaxis or therapy of one or more of the following:
  Motor neuron disease;
  Alzheimers disease;
  Muscular dystrophy;
  Peripheral neuropathies;
  Autonomic neuropathies;
  Memory loss; and
  Neurodegeneration due to aging.

Conveniently, the expression of GAD and/or its receptors is upregulated through the administration of GPE or its analogs in the prophylaxis or therapy of one or more of the following:
  postasphyxial seizures;
  convulsive disorders such as epilepsy: and
  neurodegenerative diseases such as Huntingtons.

Conveniently, the expression of NOS and/or its receptors is upregulated through the administration of GPE or its analogs in the prophylaxis or therapy of one or more of the following:
  subarachonoid haemorrahge;
  transient ischemic attack;
  stroke;
  multinfarct dementia;
  cerebral vasculitis; and
  traumatic brain injury.

In a further aspect, the invention also consists in the use of GPE or an analog thereof in the manufacture of a medicament for use in increasing the amount of ChAT, GAD or NOS present in the CNS.

BRIEF DESCRIPTION OF THE DRAWINGS

The present invention is broadly as defined above. However, those persons skilled in the art will appreciate that it is not limited only to the above but that it also includes embodiments of which the following description provides examples. A better understanding of the present invention will also be gained through reference to the accompanying drawings in which.

DESCRIPTION OF THE INVENTION

Figure 1:
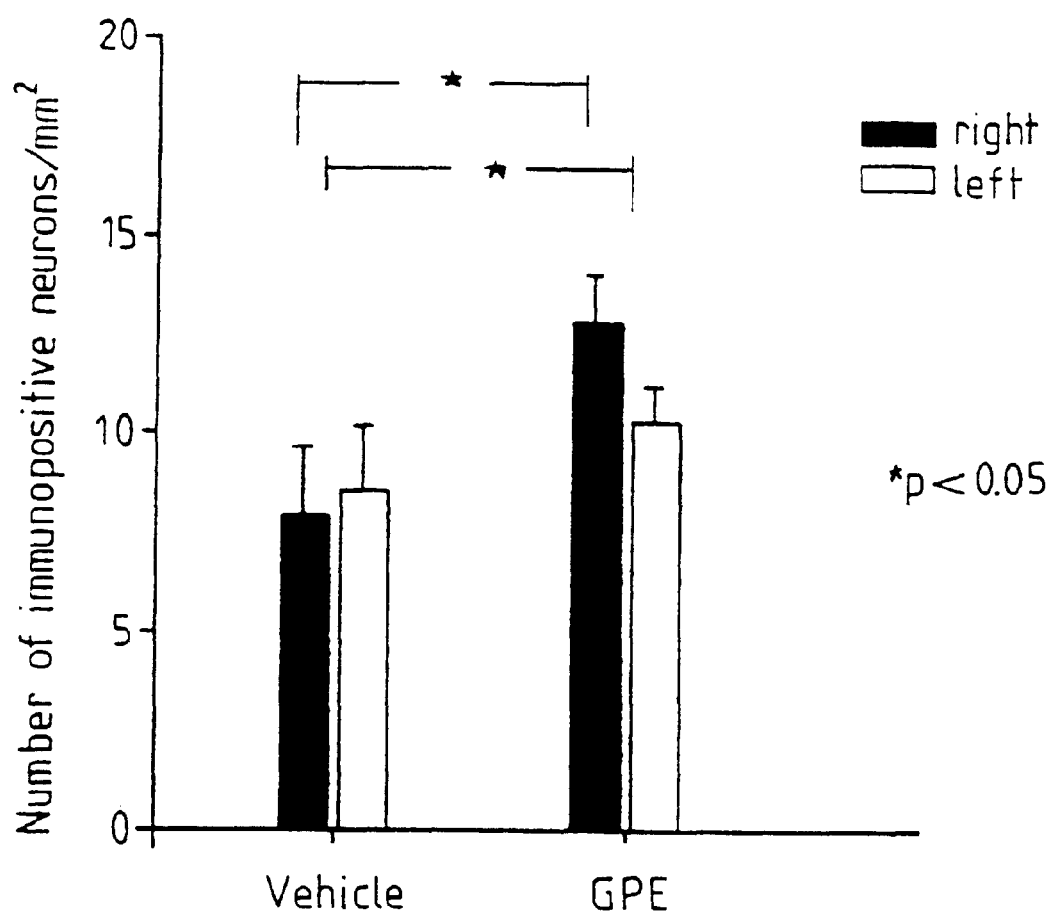
FIG. 1 shows the number of ChAT-positive neurons following treatment with a control vehicle or with 3 μg of GPE 2 hours after induced hypoxia.

As indicated above, the present invention is broadly based upon the applicants surprising finding that GPE and its analogs are capable of increasing the amount of certain neural enzymes within the CNS. This increase, which is through upregulating enzyme expression, is achieved through increasing the effective concentration or amount of GPE or the analog in the CNS of a patient. The neural enzymes specifically upregulated in effect are ChAT, GAD and NOS.

It is presently preferred by the applicants that GPE itself be used to increase the amount of the neural enzyme. Most conveniently, this is effected through the direct administration of GPE to the patient.

However, while this is presently preferred, there is no intention on the part of the applicants to exclude administration of other forms of GPE. By way of example, the effective amount of GPE in the CNS can be increased by administration of a prodrug form of GPE which comprises GPE and a carrier, GPE and the carrier being joined by a linkage which is susceptible to cleavage or digestion within the patient. Any suitable linkage can be employed which will be cleaved or digested to release GPE following administration.

It is further preferred that GPE be administered as part of a medicament or pharmaceutical preparation. This can involve combination of GPE with any pharmaceutically appropriate carrier, adjuvant or excipient. The selection of the carrier, adjuvant or excipient will of course usually be dependent upon the route of administration to be employed.

The administration route can vary widely. An advantage of GPE is that it can be administered peripherally. This means that it need not be administered directly to the CNS of the patient in order to have effect in the CNS.

Any peripheral route of administration known in the art can be employed. These can include parenteral routes with injection into the peripheral circulation being a suitable example. However, alternative administration routes selected from oral, rectal, nasal, subcutaneous, inhalation, intraperitonial or intramuscular can be employed.

Two of the most convenient administration routes will be by IV (eg. dissolved in 0.9% sodium chloride) or orally (in a capsule).

It will also be appreciated that it may on occasion be desirable to directly administer GPE to the CNS of the patient. Again, this can be achieved by any appropriate direct administration route. Examples include administration by lateral cerebro-ventricular injection or through a surgically inserted shunt into the lateral cerebro-ventricle of the brain of the patient.

The calculation of the effective amount of GPE or its analogs to be administered will be routine to those persons skilled in this art. Needless to say, the final amount to be administered will be dependent upon the route of administration and upon the nature of the neurological disorder or condition which is to be treated. A suitable dose range may for example be between about 0.04 μg to 1000 μg of GPE and/or analog per 100 g of body weight where the dose is administered centrally.

GPE and its analogs can be obtained from a suitable commercial source. Alternatively, GPE and its analogs can be directly synthesised by conventional methods such as the stepwise solid phase synthesis method of Merryfield et al. (*J. Amer. Chem. Soc.* 85 2149–2156 (1963)). Alternatively, synthesis can involve the use of commercially available peptide synthesisers such as the Applied Biosystems model 430A.

The present invention will now be illustrated with reference to the following non-limiting examples.

EXAMPLE 1

The objective of these studies was to determine the effects of administering GPE on expression of ChAT in the presence or absence of CNS injury. The experiment involved treating the rats with a control vehicle or GPE 2 hours after a focal CNS injury. These rats had an hypoxic-ischemic injury to one cerebral hemisphere induced in a standard manner (ligation of the carotid artery). The degree and length of hypoxia, the ambient temperature and humidity were defined to standardise the degree of damage. The neuronal death is restricted to the side of the carotid ligation and is primarily in the hippocarnpus, dentate gyrus, striatum and lateral cortex of the ligated hemisphere. There is no neuronal loss in the contralateral hemisphere.

Specifically, nine pairs of adult wistar rats (280–320g) were prepared under halothane/$O_2$ anaesthesia. The right side carotid artery was ligated. A guide cannula was placed on the dura 7.5 mm anterior from stereotaxic zero and 1.5 mm from midline on the right. The rats were allowed to recover for 1 hour and were then placed in an incubator with humidity 90+/−5% and temperature 31+/−0.5° C. for 1 hour before hypoxia. Oxygen concentration was reduced and maintained at 6+/−0.202% for 10 minutes. The rats were kept in the incubator for 2 hours after hypoxia and then treated either with 3 ug GPE or vehicle alone (0.1M citrate buffer [pH6], diluted 10 times in 0.1% bovine serum albumin in 0.1M phosphate buffered saline [PBS][pH7.3]). A further 6 rats were used as normal controls. The rats were sacrificed using pentobarbital 3 days after hypoxic-schemic injury. Brains were perfused with normal saline and 4% paraformaldehyde and fixed in perfusion fixative overnight. Brains were stored in 25% sucrose in 0.1M PBS (pH7.4) until the tissue sank. Frozen coronal sections (30 um) of striatum, globus pallidus and substantia nigra were cut using a microtome and stored in 0.1% sodium azide in 0.1M PBS at 4° C. Immunoreactivity for Choline acetyltransferase (ChAT) was established by staining using a free floating section method. Briefly, the antibodies were diluted in 1% goat serum. The sections were incubated in 0.2% triton in 0.1M PBS/triton at 4° C. overnight before immunohistochemistry. The sections were pre-treated with 1% $H_2O_2$ in 50% methanol for 20 minutes. The sections were then incubated with rabbit (Rb) anti-ChAT (1:5000) antibodies (the primary antibodies) in 4D on a shaker for two days. The sections were washed using PBS/triton (15 minutes×3d) and then incubated with goat anti-rabbit biotinylated secondary antibodies (1:1000) at room temperature overnight. The sections were washed and incubated in (ExtrAvidin TM Sigma 1:1000) for 3 hours and followed by $H_2O_2$ (0.01%) in 3,3-diaminobenzidine tetrahydrochloride (DAB, 0.05%) reaction. These sections were mounted on chrome alum coated slides, dried, dehydrated and covered.

The striatal neurons in both hemispheres which showed specific immunoreactivities corresponding to ChAT were counted using a light microscope and a 1 mm 2×1000 grid. The size of the striatal region used for the count was measured using an image analyser. The total counts of neurons/$mm^2$ were compared between the GPE and vehicle treated group. Data were analysed with paired t-test and presented as mean +/− sem. Results are presented in FIG. 1.

This figure shows that the number of ChAT immunopositive neurons increased in both the right and left (uninjured) sides. This clearly indicates that administration of GPE is effective to upregulate ChAT expression.

EXAMPLE 2

The objective of these studies was to determine the effects of administering GPE on expression of GAD in the presence or absence of CNS injury. The experiment involved treating the rats with a control vehicle or GPE 2 hours after a focal CNS injury. These rats had an hypoxic-ischemic injury to one cerebral hemisphere induced in a standard manner (ligation of the carotid artery). The degree and length of hypoxia, the ambient temperature and humidity were defined to standardise the degree of damage. The neuronal death is restricted to the side of the carotid ligation and is primarily in the hippocampus, dentate gyrus, striatum and lateral cortex of the ligated hemisphere. There is no neuronal loss in the contralateral hemisphere.

Specifically, nine pairs of adult wistar rats (280–320 g) were prepared under halothane/$O_2$ anaesthesia. The right side carotid artery was ligated. A guide cannula was placed on the dura 7.5 mm anterior from stereotaxic zero and 1.5 mm from midline on the right. The rats were allowed to recover for 1 hour and were then placed in an incubator with humidity 90+/−5% and temperature 31+/−0.5° C. for 1 hour before hypoxia. Oxygen concentration was reduced and maintained at 6+/−0.202% for 10 minutes. The rats were kept in the incubator for 2 hours after hypoxia and then treated either with 3 ug GPE or vehicle alone (0.1M citrate buffer [pH6], diluted 10 times in 0.1% bovine serum albumin in 0.1M phosphate buffered saline [PBS] [pH7.3]). A further 6 rats were used as normal controls. The rats were sacrificed using pentobarbital 3 days after hypoxic-schemic injury. Brains were perfused with normal saline and 4% paraformaldehyde and fixed in perfusion fixative overnight. Brains were stored in 25% sucrose in 0.1M PBS (pH7.4) until the tissue sank. Frozen coronal sections (30 um) of striatum, globus pallidus and substantia nigra were cut using a microtome and stored in 0.1% sodium azide in 0.1M PBS at 4° C. Immunoreactivity for GAD was established by staining using a free floating section method. Briefly, the antibodies were diluted in 1% goat serum. The sections were incubated in 0.2% triton in 0.1M PBS/triton at 4° C. overnight before immunohistochemistry. The sections were pre-treated with 1% $H_2O_2$ in 50% methanol for 20 minutes. The sections were then incubated with rabbit (Rb) anti-GAD (1:5000) antibodies (the primary antibodies) in 4D on a shaker for two days. The sections were washed using PBS/triton (15 minutes×3 d) and then incubated with goat anti-rabbit biotinylated secondary antibodies (1:1000) at room temperature overnight. The sections were washed and incubated in (ExtrAvidin TM Sigma 1:1000) for 3 hours and followed by $H_2O_2$ (0.01%) in 3,3-diaminobenzidine tetrahydrochloride (DAB, 0.05%) reaction. These sections were mounted on chrome alum coated slides, dried, dehydrated and covered.

Figure 2:
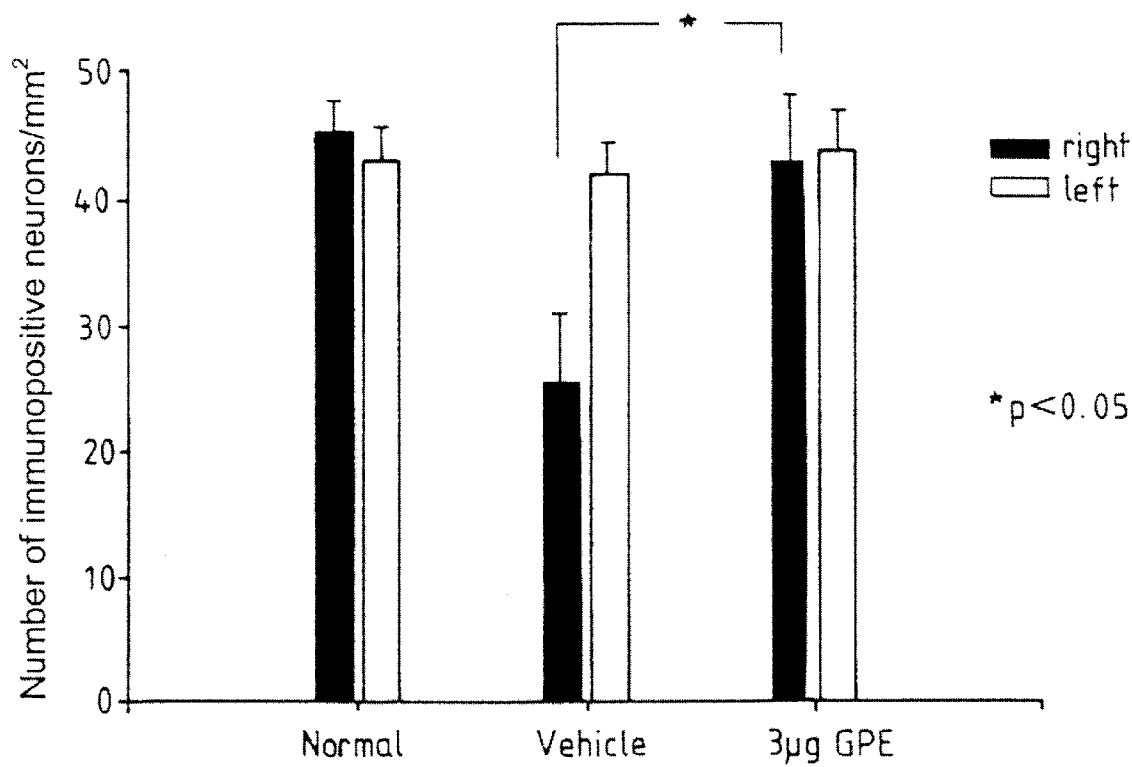
FIG. 2 shows the number of GAD-positive neurons following treatment with a control vehicle or with 3 μg of GPE 2 hours after induced hypoxia.

The striatal neurons in both hemispheres which showed specific immunoreactivities corresponding to GAD were counted using a light microscope and a 1 mm 2×1000 grid. The size of the striatal region used for the count was measured using an image analyser. The total counts of neurons/$mm^2$ were compared between the GPE and vehicle treated group. Data were analysed with paired t-test and presented as mean +/− sem. Results are presented in FIG. 2.

This figure shows that the number of GAD immunopositive neurons increased in the right side whereas Paravalbumin (a marker for the same cell type) was not increased, showing that GAD expression was upregulated in the surviving cells (*$p<0.05$).

EXAMPLE 3

The objective of these studies was to determine the effects of administering GPE on expression of NOS in the presence or absence of CNS injury. The experiment involved treating the rats with a control vehicle or GPE 2 hours after a focal CNS injury. These rats had an hypoxic-ischemic injury to one cerebral hemisphere induced in a standard manner (ligation of the carotid artery). The degree and length of hypoxia, the ambient temperature and humidity were defined to standardise the degree of damage. The neuronal death is restricted to the side of the carotid ligation and is primarily in the hippocampus, dentate gyrus, striatum and lateral cortex of the ligated hemisphere. There is no neuronal loss in the contralateral hemisphere.

Specifically, nine pairs of adult wistar rats (280–320 g) were prepared under halothane/$O_2$ anaesthesia. The right side carotid artery was ligated. A guide cannula was placed on the dura 7.5 mm anterior from stereotaxic zero and 1.5 mm from midline on the right. The rats were allowed to recover for 1 hour and were then placed in an incubator with humidity 90+/−5% and temperature 31+/−0.5° C. for 1 hour before hypoxia. Oxygen concentration was reduced and maintained at 6+/−0.202% for 10 minutes. The rats were kept in the incubator for 2 hours after hypoxia and then treated either with 3 ug GPE or vehicle alone (0.1M citrate buffer [pH6], diluted 10 times in 0.1% bovine serum albumin in 0.1M phosphate buffered saline [PBS][pH7.3]). A further 6 rats were used as normal controls. The rats were sacrificed using pentobarbital 3 days after hypoxic-schemic injury. Brains were perfused with normal saline and 4% paraformaldehyde and fixed in perfusion fixative overnight. Brains were stored in 25% sucrose in 0.1M PBS (pH7.4) until the tissue sank. Frozen coronal sections (30 um) of striatum, globus pallidus and substantia nigra were cut using a microtome and stored in 0.1% sodium azide in 0.1M PBS at 4° C. Immunoreactivity for neuronal nitric oxide synthetase (NOS) was established by staining using a free floating section method. Briefly, the antibodies were diluted in 1% goat serum. The sections were incubated in 0.2% triton in 0.1M PBS/triton at 4° C. overnight before immunohistochemistry. The sections were pre-treated with 1% $H_2O_2$ in 50% methanol for 20 minutes. The sections were then incubated with rabbit (Rb) anti-NOS (1:3000) antibodies (the primary antibodies) in 4D on a shaker for two days. The sections were washed using PBS/triton (15 minutes×3 d) and then incubated with goat anti-rabbit biotinylated secondary antibodies (1:1000) at room temperature overnight. The sections were washed and incubated in (ExtrAvidin TM Sigma 1:1000) for 3 hours and followed by $H_2O_2$ (0.01%) in 3,3-diaminobenzidine tetrahydrochloride (DAB, 0.05%) reaction. These sections were mounted on chrome alum coated slides, dried, dehydrated and covered.

Figure 3:
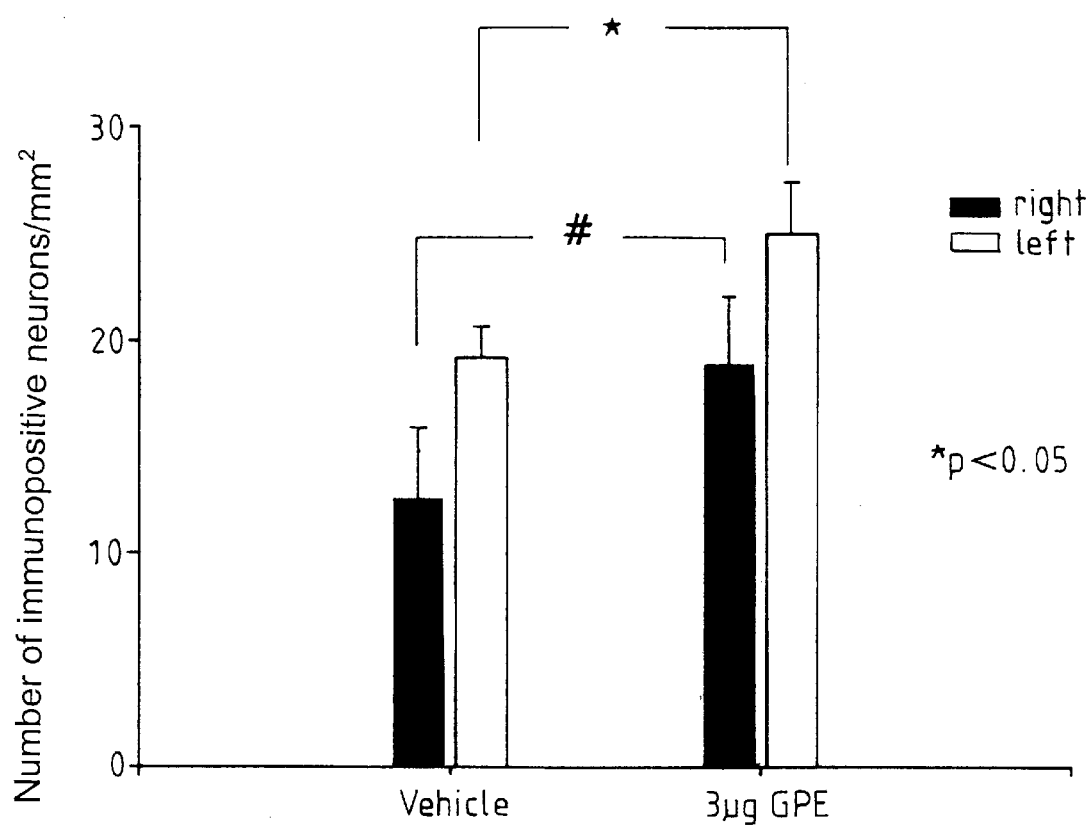
FIG. 3 shows the number of NOS-positive neurons following treatment with a control vehicle or with 3 μg of GPE 2 hours after induced hypoxia.

The striatal neurons in both hemispheres which showed specific immunoreactivities corresponding to NOS were counted using a light microscope and a 1 mm 2×1000 grid. The size of the striatal region used for the count was measured using an image analyser. The total counts of neurons/mm$^2$ were compared between the GPE and vehicle treated group. Data were analysed with paired t-test and presented as mean +/− sem. Results are presented in FIG. 3.

This figure shows that the number of NOS immunopositive neurons increased in both the right and left (uninjured) sides (#p=0.072, *p=0.008). This clearly indicates that administration of GPE is effective to upregulate NOS expression.

EXAMPLE 4

The objective of this study was to determine the effect of GPE administration on the expression of GAD, NOS and ChAT in the presence or absence of injury to the striatum induced by quinolinic acid. When injected into the striatum in experimental animals quinolinic acid produces lesions arising from the loss of striatopallidal and striatonigral GABAergic projection neurons, but spares the axons in the striatum (*Science*, 219, 316–318 [1983]). Rats were either treated with a control vehicle or GPE 2 hours after administration of quinolinic acid.

Materials and Methods

A total of 14 adult male Wistar rats (280–310 g) were used in this investigation. Eight rats were anaesthetized using halothane/$O_2$ anaesthesia. An injection of quinolinic acid (78 units, Sigma, dissolved in 4M NaOH) was stereotaxically placed in the dorsal region of the right striatum 0.8 mm anterior to bregma, 2.5 mm lateral to the midline and 4.0 mm ventral to the pial surface. 2 hours later an injection of 3 μg GPE or vehicle alone (0.1M citrate buffer [pH6], diluted 10 times in 0.1% bovine serum albumin in 0.1M phosphate buffered saline [PBS][pH7.3]) was administered into the right lateral ventrical via a guide cannula 7.5 mm anterior from stereotaxic zero, 1.5 mm from the midline on the right, and vertical 3 mm. Six rats were used as normal controls.

The rats were sacrificed using pentobarbitol 3 days after the quinolinic acid induced striatal injury. Brains were perfused with 10% buffered formalin (pH7) and processed for immunoreactivity for GAD, NOS which are found in GABAergic interneurons in the striatum and ChAT, which synthesizes acetylcholine and is found in cholinergic neurons in the striatum. Brains were stored in 25% sucrose in 0.1M PBS (pH7.4) until the tissue sank. Frozen coronal sections (30 μm) of the striatum, globus pallidus and substantia nigra were cut using a microtome and stored in 0.1% sodium azide in 0.1M PBS at 4° C. Immunoreactivity for GAD, NOS and ChAT was established by staining using a free floating method. Briefly, the antibodies were diluted in 1% goat serum. The sections were incubated in 0.2% triton in 0.1M PBS/triton at 4° C. overnight before immunohistochemistry. The sections were pre-treated with 1% $H_2O_2$ in 50% methanol for 20 minutes. The sections were then incubated either with rabbit anti-GAD (1:5000), rabbit anti-NOS (1:3000) or rabbit anti-ChAT (1:5000) in 4D on a shaker for two days. The sections were washed using PBS/triton (15 minutes×3) and then incubated with goat anti-rabbit biotinylated secondary antibodies (1:1000, Amersharn) at room temperature overnight. Sections were washed and incubated in (ExtrAvidin™, 1:1000, Sigma) for 3 hours and then reacted in 0.05% 3,3-diaminobenzidine tetrahydrochloride and 0.01% $H_2O_2$ to produce a brown reaction product. These sections were mounted on chrome alum coated slides, dried, dehydrated and covered.

The striatal neurons in both hemispheres which showed specific immunoreactivities corresponding to GAD, NOS and ChAT were counted using a light microscope and a 1 mm 2×1000 grid. The size of the striatal region used for the count was measured using an image analyser (Mocha image analysis software). The total counts of neurons/mm$^2$ were compared between the GPE and vehicle treated group. The data has not been analysed for statistical signigicance. Tissue from one of the GPE treated animals was unable to be counted. These results are presented in FIGS. 4–6.

Results

Figure 4:
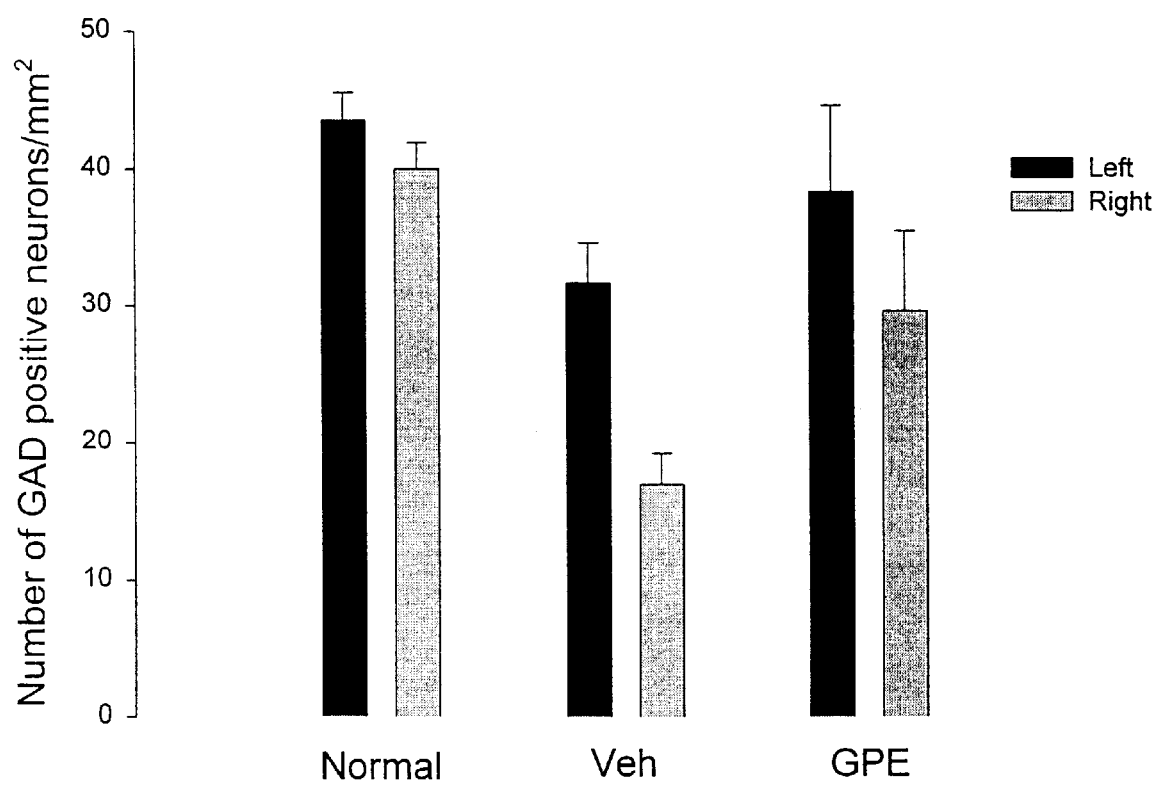
FIG. 4 shows the effects of GPE on the number of GAD-positive neurons following quinolinic acid-induced injury to the brain.

FIG. 4 shows a loss of GAD immunoreactivity in the striatum on both the left (non-injured) and right sides of the brain following injury. GPE induced an upregulation of GAD expression on both sides of the brain.

Figure 5:
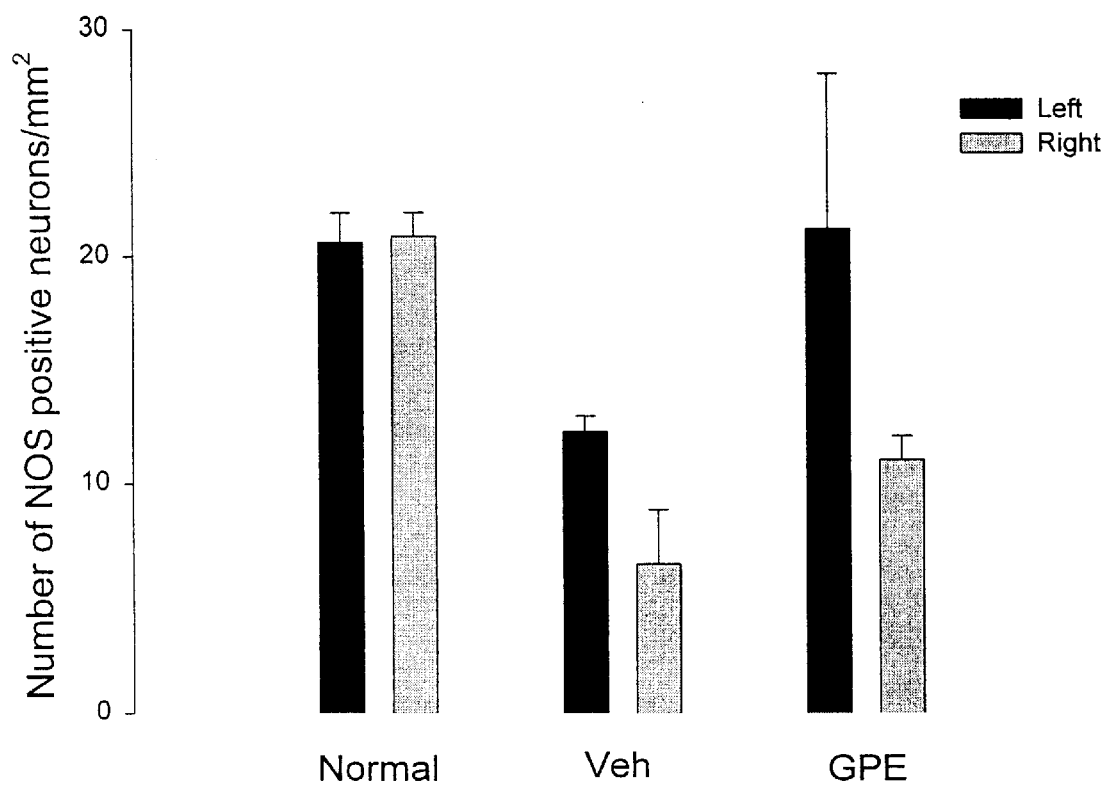
FIG. 5 shows the effects of GPE on the number of NOS-positive neurons following quinolinic acid-induced injury to the brain.

FIG. 5 shows a loss of NOS activity in the striatum after injury on both the left and right sides of the brain. GPE induced an upregulation of enzyme expression on both sides of the brain, restoring the enzyme levels to normal on the left (non-injured) side of the brain.

Figure 6:
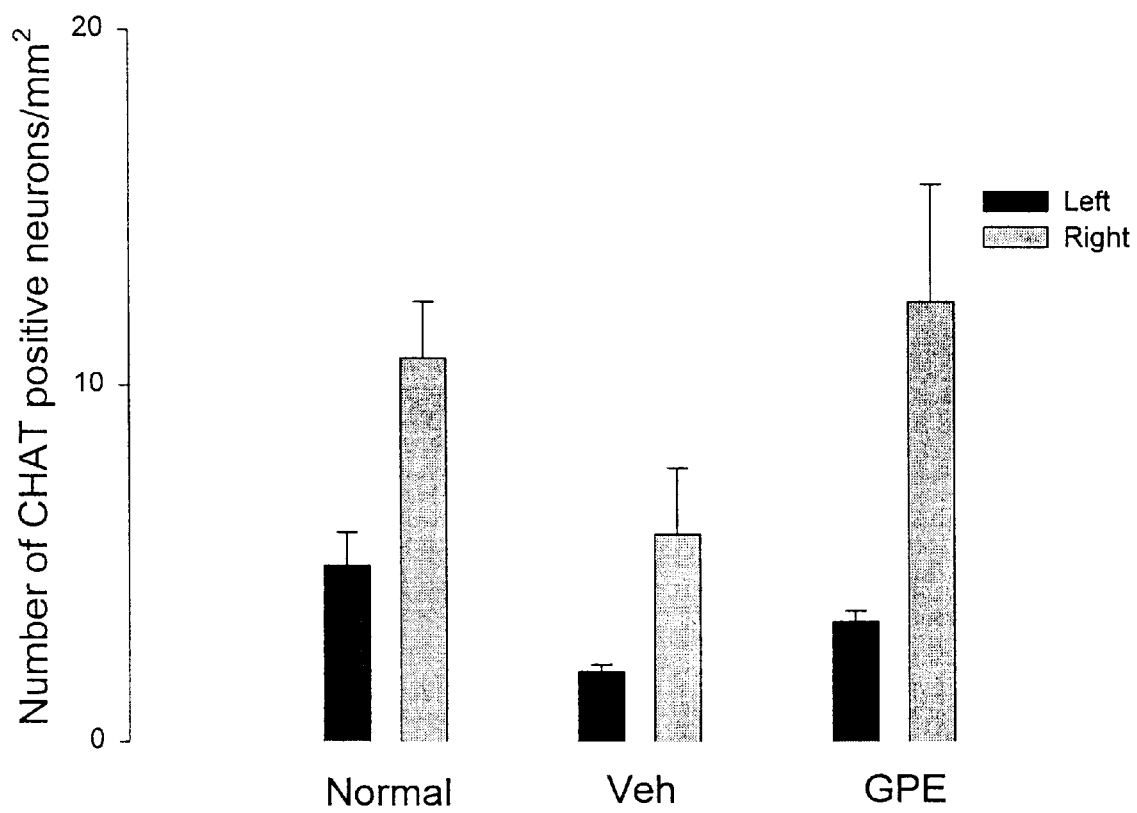
FIG. 6 shows the effects of GPE on the number of ChAT-positive neurons following quinolinic acid-induced injury to the brain.

FIG. 6 shows a loss of ChAT immunoreactivity after injury on both sides of the brain. GPE treatment upregulated the levels of ChAT to above normal on the right (injured) side of the brain.

Conclusions

These results demonstrate the ability of GPE to regulate the expression of GAD, NOS and ChAT in the CNS.

Furthermore, the results indicate that GAD and NOS are regulated in the presence and absence of the quinolinic acid induced injury. This clearly demonstrates the effect of GPE in upregulating GAD and NOS expression independent of a response to neural damage or a threat to neural cell survival.

The results also show that ChAT can be upregulated by GPE in the presence of quinotinic acid induced neural injury.

Industrial Application

The experimental results demonstrate the ability of GPE to increase the amount of the neural enzymes ChAT, GAD and NOS in the CNS through a direct increase in enzyme expression. Further, the results indicate that expression of both ChAT and NOS is upregulated both in the presence and absence of neural injury. This clearly represents that the effect of GPE in upregulating expression of these enzymes is independent of a response to neural damage or a threat to neural cell survival.

These findings make GPE and its analogs applicable in treating a number of neurological disorders or conditions, either therapeutically or prophylactically. Indeed, it will be apparent to those persons skilled in the art that GPE and its analogs can be employed at any time where a patient would benefit from an increase in the expression of ChAT, GAD or NOS within the CNS. Neurological disorders or conditions which would benefit from this include, but are not limited to the following:

motor neuron disease, Alzheimers disease, muscular dystrophy, peripheral neuropathies, autonomic neuropathies, memory loss, aging and other forms of neurodegeneration (ChAT);

postasphyxial seizures, epilepsy and other convulsive disorders, neurodegenerative diseases such as Huntingtons, plus the immediate post acute phase following head trauma, stroke, and other forms of hypoxic ischemic brain injury (GAD); and subarachonoid haemorrahge, transient ischemic attack, stroke, multinfarct dementia, cerebral vasculitis and traumatic brain injury plus the immediate post acute phase following head trauma, stroke and other forms of hypoxic ischemic brain injury.

it will be appreciated that although the present invention is described above with reference to certain specific embodiments, the description provided is exemplary only and that the invention is limited only by the lawful scope of the appended claims.

What is claimed is:

1. A method of treatment of a patient suffering from or susceptible to a condition in which the amount of a neural enzyme selected from NOS and GAD is reduced, which method comprises the step of increasing the effective amount of GPE or an analog thereof within the CNS of said patient by administration of a dose of GPE or an analog or prodrug thereof in a dosage range of between about 0.04 $\mu$g per 100 g of body weight to about 0.1 $\mu$g per 100 g of body weight.

2. A method of treatment as claimed in claim 1, wherein the concentration of GPE is increased in the CNS by direct administration of GPE.

3. A method according to claim 1 which is prophylactic.

4. A method according to claim 1 which is therapeutic.

5. A method of treatment of a patient suffering from or susceptible to motor neuron disease comprising the step of increasing the effective amount of GPE or an analog or prodrug thereof within the CNS of said patient by administration of a dose of GPE or an analog thereof in a dosage range of between about 0.04 $\mu$g per 100 g of body weight to about 0.1 $\mu$g per 100 g of body weight.

6. A method according to claim 1 wherein the condition is one in which the amount of GAD is reduced.

7. A method according to claim 1 wherein the condition is one in which the amount of NOS is reduced.

8. A method according to claim 1 wherein said condition is cerebral vasculitis.

9. A method of upregulating the expression of the neural enzyme GAD in a mammal in need thereof, said method comprising the step of increasing the effective amount of GPE or an analog or prodrug thereof within the CNS of said mammal by administration of a dose of GPE or an analog or prodrug thereof in a dosage range of between about 0.04 ug per 100 g of body weight to about 0.1 ug per 100 g of body weight.

10. A method of upregulating the expression of the neural enzyme NOS in a patient mammal in need thereof, said method comprising the step of increasing the effective amount of GPE or an analog or prodrug thereof within the CNS of said mammal by administration of a dose of GPE or an analog or prodrug thereof in a dosage range of between about 0.04 ug per 100 g of body weight to about 0.1 ug per 100 g of body weight.

11. A method of treatment of a condition in which the amount of a neural enzyme selected from GAD and NOS is reduced comprising the steps of a) preparation of a medicament comprising GPE or an analog or prodrug thereof and b) administration of the medicament within the CNS of a patient in need thereof in a dosage range of between about 0.04 $\mu$g per 100 g of body weight to about 0.1 $\mu$g per 100 g of body weight for therapeutic or prophylactic purposes.

12. The method of claim 11 wherein the condition comprises one in which the expression of GAD is reduced in the CNS of a patient.

13. The method claim 11 wherein the condition comprises one in which the expression of NOS is reduced in the CNS of a patient.

14. A method according to claim 9 which comprises direct administration of GPE, an analog thereof or a prodrug thereof to the CNS of said mammal.

15. A method according to claim 10 which comprises direct administration of GPE, an analog thereof or a prodrug thereof to the CNS of said mammal.

16. The method of claim 12, wherein the medicament is administered for prophylactic purposes.

17. The method of claim 13, wherein the medicament is administered for prophylactic purposes.

18. The method of claim 1, wherein the condition in which the neural enzyme is reduced is not the result of severe neural injury or degeneration.

* * * * *

UNITED STATES PATENT AND TRADEMARK OFFICE
CERTIFICATE OF CORRECTION

PATENT NO. : 6,365,573 B1
DATED : April 2, 2002
INVENTOR(S) : Gluckman et al.

It is certified that error appears in the above-identified patent and that said Letters Patent is hereby corrected as shown below:

Column 10,
Lines 6 and 7, after the numbers 0.04 and 0.1 "ug" should read -- $\mu$g --.
Line 10, please remove the word "patient".
Lines 15 and 16, after the numbers 0.04 and 0.1 "ug" should read -- $\mu$g --.

Signed and Sealed this

Eighth Day of October, 2002

Attest:

Attesting Officer

JAMES E. ROGAN
*Director of the United States Patent and Trademark Office*